United States Patent
Hsiung et al.

(10) Patent No.: US 7,164,162 B2
(45) Date of Patent: Jan. 16, 2007

(54) METHOD FOR FORMING POTASSIUM/SODIUM ION SENSING DEVICE APPLYING EXTENDED-GATE FIELD EFFECT TRANSISTOR

(76) Inventors: Shen-Kan Hsiung, No. 22, Puren Li, Jungli City, Taoyuan (TW); Jung-Chuan Chou, No. 23, Lane 125, Sec. 3, Dasyue Rd., Douliou City, Yunlin County (TW); Tai-Ping Sun, 8F., No. 949, Yongfu Rd., Jhongli City, Taoyuan County (TW); Chung-We Pan, No. 77, Lane 128, Neighborhood 2, Paotso Village, Wandan Township, Pingtung County (TW); I-Kone Kao, No. 15, Lane 191, Sec. 3, Mincyuan E. Rd., Taipei City, Songshan District (TW)

( * ) Notice: Subject to any disclaimer, the term of this patent is extended or adjusted under 35 U.S.C. 154(b) by 89 days.

(21) Appl. No.: 10/891,569

(22) Filed: Jul. 15, 2004

(65) Prior Publication Data

US 2006/0011951 A1 Jan. 19, 2006

(51) Int. Cl.
*H01L 21/335* (2006.01)
(52) U.S. Cl. .................... 257/253; 257/414; 257/E21.4
(58) Field of Classification Search ................ 257/225, 257/253, 414
See application file for complete search history.

(56) References Cited

U.S. PATENT DOCUMENTS

| 4,060,426 A * | 11/1977 | Zinchuk ..................... 136/263 |
| 4,200,472 A * | 4/1980 | Chappell et al. ............. 136/246 |
| 6,559,474 B1 * | 5/2003 | Craighead et al. ............ 257/40 |
| 2003/0196477 A1 * | 10/2003 | Auner et al. ................ 73/24.06 |
| 2004/0256685 A1 * | 12/2004 | Chou et al. .................. 257/414 |

OTHER PUBLICATIONS

Yin et al.; Study of indium tin oxide thin film for separative extended gate ISET; Mater. Chem. Phys.; vol. 70; pp. 12-16; 2001.*
Pan et al.; Using polypyrrole as the contrast pH detector to fabricate a whole solid-state pH sensing device; Sensors Journal, IEEE; vol. 3, Issue 2; Apr. 2003; pp. 164-170.*

* cited by examiner

*Primary Examiner*—Marcos D. Pizarro
(74) *Attorney, Agent, or Firm*—Rosenberg, Klein & Lee (57) ABSTRACT

A potassium/sodium ion sensing device applying an extended-gate field effect transistor, which using an extended-gate ion sensitive field effect transistor (EGFET) as base to fabricate a potassium/sodium ion sensing device, using the extended gate of the extended-gate ion sensitive field effect transistor as a signal intercept electrode, and immobilizing the hydro-aliphatic urethane diacrylate (EB2001) intermixed with electronegative additive, potassium ionophore, sodium ionophore, and the like, to fabricate a potassium/sodium ion sensing electrode. The present invention utilizes the photocurability and good hydrophilicity of the hydro-aliphatic urethane diacrylate (EB2001), and fixes potassium/sodium ionophore, can obtain a non-wave filter, single-layer, stable signal potassium and sodium ion sensor. Thus, when the present invention is applied to measure the concentration of potassium/sodium ions in a sample, the mutual interference between potassium/sodium ion electrodes can be reduced, so the measured value can be more close to the actual value.

11 Claims, 7 Drawing Sheets

METHOD FOR FORMING POTASSIUM/SODIUM ION SENSING DEVICE APPLYING EXTENDED-GATE FIELD EFFECT TRANSISTOR

BACKGROUND OF THE INVENTION

1. Field of the Invention

The present invention relates to a potassium/sodium ion sensing device applying an extended-gate field effect transistor, particularly to a potassium/sodium ion sensing device applying an extended-gate field effect transistor which uses an ion interference for mutual correction to obtain more accurate values. Therefore, the present invention can be applied to industries such as medical examinations, bio-medical materials, and semiconductor device fabrications, etc.

2. Description of the Prior Art

As compared with conventional ion selective glass electrodes, at present the solid-state electrode has more advantages, such as low cost, easy miniaturization and durability, non-breakable, etc., therefore the market share is tend to ripe semiconductor integration of field effect transistor substitute for conventional glass electrode. [P. Bergveld, "Development of an ion-sensitive solid-state device for neurophysiological measurements", IEEE Transactions on Biomedical Engineering, BME-17, pp. 70–71, 1970].

The fluid of a human body can be classified to extra-cellular and intra-cellular fluids, wherein primary ions include sodium, potassium, calcium, etc.; the balance of sodium ion and potassium ion is important particularly. In the normal condition of a human body, the concentration of sodium/potassium ions is stable, the normal value of serum potassium is 3.5–5.0 mM(avg. 4.3 mM), the normal value of serum sodium is 135–145 mM(avg. 140 mM)[pp. 847–900, Sec. 2 Examination, The Clinical Internal Medicine, BOR-SHEN HSIEH, published by Golden Name Press, 1990]. Thus, sodium is a major cation in the extra-cellular fluid of a human body, 98% ion is sodium ion in all extracellular, and 2% ion is sodium ion in all intra-cellular. The potassium and sodium ion concentration will change if a patient has kidney failure or dehydration, thus the doctor can use the unbalance condition of sodium/potassium ions to examine the disease of the human body. The determination of content of sodium/potassium ions in the human body is generally performed by polarographic method, atomic absorption spectrometry (AAS), and the like which need pre-processing and operating inconveniently. Those current commercial pH/sodium/potassium ion electrodes often have errors when used to measure the environment of interfering ion more than the measured ion (that is, the extra-cellular and intra-cellular fluids in the human body). Thus, in order to remove the interference from various ions on electrodes, it is required to measure the ions having greater effects in the solution simultaneously.

Patents related to the conventional technology are described as follows:

(1) Inventor: D. C. Chan Andy, Patent Number: U.S. Pat. No. 6,416,646; Date of patent: Jul. 9, 2002, Title: "Method of making a material for establishing solid state contact for ion selective electrodes". This cited reference discloses a polymeric material, a methacrylamidopropyltrimethyl-ammoniumchloride (MAPTAC) or methyllmethacrylate (MMA), applied on the gate of a field effect transistor to fabricate an ion selective electrode, which is stable and reproducible, and polymeric membrane mixable with ion selective material being incorporated in a solid-state electrode; The electric charge of the polymer described in the cited reference is 2.72 mEq/g (millaequivalents/gram), and the polymeric material recited in the claims includes immobilized sites of charge opposite that of mobile ions involved in the redox couple.

(2) Inventor: Martijn Marcus Gabriel Antonisse, David Nicolaas Reinhoudt, Bianca Henriette Maria Snellink-Ruel, Peter Timmerman, Patent Nubmer: U.S. Pat. No. 6,468,406. Date of patent. Oct. 22, 2002, Title: "Anion-complexing compound, method of preparing the same, an ion-selective membrane and a sensor provided with such a compound or membrane". This cited reference discloses the synthesis and application of an ion selective material of alkali and alkaline earth group, using organic synthesis, to prepare compounds with specific functional group; such as —NHC(X)—, —C(X)NH—, —NHC(X)NH—, wherein X includes sulfur or oxygen atom, with its specific compound structure, to achieve the effect for selecting an ion selective material of alkali and alkaline earth group; the cited reference also discloses, adding on a polymer to encapsulate an ion selective material, to prepare an extended gate ion selective electrode.

(3) Inventor: Massimo Battilotti, Giuseppina Mazzamurro, Matteo Giongo, Invent Number: U.S. Pat. No. 5,130,265. Date of patent. Dec. 21, 1989, Title: "Process for obtaining a multifunctional, ion-selective-membrane sensor using a siloxanic prepolymer". This cited reference discloses a process, using a photocurable polymer, to achieve fixing various ion selective materials on a microelement. A claimed process of a sensing device, which using a solvent with a photoinitiator to solve silica and an ion selective material, applied to a substrate in liquid using spinning, and then exposed with appropriate ultraviolet light, after cleaned by an organic solvent, hardening the polymer by heating, and repeating the above, to obtain a sensing electrode in the same substrate, and thus making various ion field effect transistor sensing devices.

(4) Inventor: Akihiko Mochizuki, Hideyo Iida, Patent Nubmer: U.S. Pat. No. 4,921,591. Date of patent. May 1, 1990, Title: "Ion sensors and their divided parts". This cited reference discloses an ion selective membrane, includes a vinyl polymer based compound containing a hydroxyl and/or carboxyl group, fixed on an extended gate sensitive field effect transistor. In the claims, it also discloses a reference electrode arranged in the opposite side of a ion selective electrode. The ion selective electrode and reference electrode are separate. The materials of reference electrode is different with the extended gate.

(5) Inventor: Noboru Oyama, Takeshi Shimomura, Shuichiro Yamaguchi, Patent Number: U.S. Pat. No. 4,816,118. Date of patent. Mar. 28, 1989, Title: "Ion-sensitive FET sensor". This cited reference discloses an ion selective electrode (ISFET), the gate of MOSFET is pulled out, and an ion selective membrane is added; wherein a redox layer having a redox function is provided between the isolating membrane and the ion-sensitive layer to improve operating stability and speed of response; an electrically conductive layer or a combination of a metal film and an electrically conductive layer is provided between the isolating membrane and the redox layer to further improve operating stability, the adhesion of the layers and the durability of the sensor. Also disclosed are optimum materials for use as an ion carrier employed in the ion-sensitive layer.

(6) Inventor: D. N. Reinhoudt, M. L. M. Pennings, A. G. Talma, Paten Number: U.S. Pat. No. 4,735,702. Date of patent. Apr. 5, 1988, Title: "Method of producing an ISFET and same ISFET". This cited reference discloses: a method of modifying an oxide surface of a semi-conductor material, incorporated for example in an ISFET, in which a polymer coating is applied to the oxide surface. This cited reference also describes: using a modified polymer to fix oxide functional group to the gate of a field effect transistor or to introduce a metal complex into a polymer, and thus to achieve a product for mass production.

Furthermore, since the miniaturization of an optical ion sensor is difficult, although electrical ion sensor can use an integrated circuit process to achieve miniaturization, the sensitive potential signal is subjected to the ion movement in the solution to produce noise. In order to stabilize the potential signal or improve potential interference, generally can add a filter circuit at the back end circuit, or as the above-cited reference (1)–(6), can change the feature of polymer of the ion selective membrane. And, according to the literatures: [IUPAC, "Recommendations for nomenclature of ion-selective electrodes", Pure and Applied Chemistry, Vol. 66, pp. 2527–2536, 1994. R. Eugster, P. M. Gehrig, W. E. Morf, U. E. Spichiger, and W. Simon, "Selectivity-modifying influence of anionic sites in neutral carrier-based membrane electrodes", Analytical Chemistry, Vol. 63, pp. 2285–2289, 1991. M. Yanming and E. Bakker, "Determination of complex formation constants of lipophilic neutral ionophores in solvent polymeric membranes with Segmented sandwich membranes", Analytical Chemistry, Vol. 71, pp. 5279–5287, 1999. S. Amemiya, P. Bulhlmann, E. Pretsch, B. Rusterholz, Y. Umezawa, "Cationic or anionic Sites-selectivity optimization of ion-selective electrodes based on charged ionophores", Analytical Chemistry, Vol. 72, pp. 1618–1631, 2000. E. Bakker, E. Pretsch, "Ion-selective electrodes based on two competitive ionophores for determining effective stability constants of ion-carrier complexes in solvent polymeric membranes", Analytical Chemistry, Vol. 70, pp. 395–302, 1998. F. Deyhimi, "A method for the determination of potentiometric selectivity coefficients of ion selective electrodes in the presence of several interfering ions", Talanta, Vol. 50 (5), pp. 1129–1134, 1999. E. Bakker, "Origin of anion response of solvent polymeric membrane based silver ion-selective electrodes", Sensors and Actuators B, Vol. 35 (1–3), pp. 20–25, 1996. P. Kane, D. Diamond, "Determination of ion-selective electrode characteristics by non-linear curve fitting", Talanta, Vol. 44, pp. 1847–1858, 1997], ion interference is: when the solution to be tested contains other ion not to be tested, the amount of the ion not to be tested can affect the output potential, so the output potential can not indicate correct concentration of the ion to be tested. However, using polymer for fixing is a special subject, different polymers will affect the ion diffusivity and ionophore encapsulatement [C. P. Hauser, W. L. D. Chiang, A. W. Graham, "A potassium ion selective electrode with valinomycin based poly (vinyl chloride) membrane and a poly (vinyl ferrocene) solid contact", Analytical Chimica Acta., Vol. 302, pp. 241–248, 1995. B. Andrey, A. Nataliya, M. Javier, D. Carlos, "Optimization of photocurable polyurethane membrane composition for ammonium ion sensor", Journal of Electrochemical Soc., Vol. 144 (2), pp. 617–621, 1997. Y. H. Lee, A. H. Hall Elizabeth, "Methacrylate-acrylate based polymers of low plasticiser cont for potassium ion-selective membranes" Analytical Chemica Acta., Vol. 324, pp. 47–56, 1996. B. Jundrey, A. Nataliya, M. Javier, D. Carlos, A. Salvador, B. Jordi "Photocureable polymer matrices for potassium-sensitive ion selective electrode membranes" Analytical Chemistry, Vol. 67, pp. 3589–3595, 1995 Yook-Heng Lee, A. H. Elizabeth, "Assessing a photocured self-plasticised acrylic membrane recipe for Na and K ion selective electrodes", Analytica Chimica Acta, Vol. 443, pp. 25–40, 2001. K. J. Shinichi, M. S. Arakawa, S. Michiko, O. Tetsuya, S. lkuo, "Flow injection analysis of potassium using an all-solid-state potassium selective electrode as a detector", Talanta, Vol. 46, pp. 1293–1297, 1998. P. C. Pandey, R. Prakash, "Polyiudole modified potassium ion sensor using dibenzo-18-crown-6 mediated PVC matrix membrane", Sensors and Actuators B, Vol. 46, pp. 61~65, 1998. M. J. Roger, P. J. S. Barbeiva, A. F. B. Sene, N. R. Stradiotto, "Potentiometria determination of potassium cations using a nickel(II) hexacyanofereate-modified electrode", Talanta, Vol. 49, pp. 271–275, 1999]. The amount of negative charge ionophore and additive influence the potentiometric selectivity coefficient in potassium/sodium ion electrodes [R. Eugster, P. M. Gehrig, W. E. Morf, U. E. Spichiger, and W. Simon, "Selectivity-modifying influence of anionic sites in neutral carrier-based membrane electrodes", Analytical Chemistry, Vol. 63, pp. 2285–2289, 1991. S. Amemiya, P. Bulhlmann, E. Pretsch, B. Rusterholz, Y. Umezawa, "Cationic or anionic Sites-selectivity optimization of ion-selective electrodes based on charged ionophores", Analytical Chemistry, Vol. 72, pp. 1618–1631, 2000], in a potassium/sodium ion sensor, if the ionosphere or electronegative additive is larger than a certain amount, the positive charge of other ions to be tested will be affected by electronegativity. Addressing to the problem of potential interference, the International Union of Pure and Applied Chemistry (IUPAC) had recommended the potential interference parameters of a potentiometric sensor [IUPAC, "Recommendations for nomenclature of ion-selective electrodes", Pure & Applied Chemistry, Vol. 66, pp. 2527–2536, 1994], potantiometric selectivity coefficient can input The Nikolsky-Eisenman equation to obtain more accurate potassium/sodium ion concentration in practice.

Accordingly, it can be seen that the above-described conventional technique still has many drawbacks, are not designed well, and thus need to be improved.

In view of disadvantages derived from the above-described conventional techniques, the present inventor had devoted to improve and innovate, and, after studying intensively for many years, developed successfully a potassium/sodium ion sensing device applying an extended-gate field effect transistor according to the invention.

SUMMARY OF THE INVENTION

The object of the invention is to provide a potassium/sodium ion sensing device applying an extended-gate field effect transistor that uses the hydro-aliphatic urethane diacrylate (EB2001) as immobile material capable of simplifying a process for fabricating an ion selective membrane to obtain a single layer membrane potassium/sodium ion sensor without an add-on wave filter circuit.

A further object of the present invention is to provide a potassium/sodium ion sensing device applying an extended-gate field effect transistor that uses a process which comprising: use realized tin oxide ($SnO_2$) as substrate and then is adhered with potassium/sodium ion selective membrane, measure the concentration potential of each ion, input known potentiometric sensitivity coefficient to the Nikolsky-Eisenman equation to reduce interference, and obtain the actual value.

Another object of the present invention is to provide a potassium/sodium ion sensing device applying an extended-gate field effect transistor with a fabrication method possessing advantages such as simple equipment, low cost, mass production, etc., thus the potassium ion and sodium ion sensing device according to the present invention has high feasibility and high applicability.

The potassium/sodium ion sensing device applying an extended-gate field effect transistor capable of achieving the above-mentioned objects, based on an extended-gate ion sensitive field effect transistor, using the extended gate of the extended-gate ion sensitive field effect transistor as a signal intercept electrode, and immobilizing the hydro-aliphatic urethane diacrylate (EB2001) intermixed with electronegative additive, ionophores such as potassium, sodium, etc., to fabricate a potassium/sodium ion sensing electrode. The present invention utilizes the photocurability and good hydrophilicity of the hydro-aliphatic urethane diacrylate (EB2001), and fixes potassium/sodium ionophore, can obtain a non-wave filter, single-layer, stable signal potassium and sodium ion sensor. Thus, when the present invention is applied to measure the concentration of potassium/sodium ions in a sample solution, the mutual interference between potassium/sodium ion electrodes can be reduced, so the measured value can be more close to the actual value.

These features and advantages of the present invention will be fully understood and appreciated from the following detailed description of the accompanying Drawings.

DETAILED DESCRIPTION OF THE PREFERRED EMBODIMENT

Figure 1:
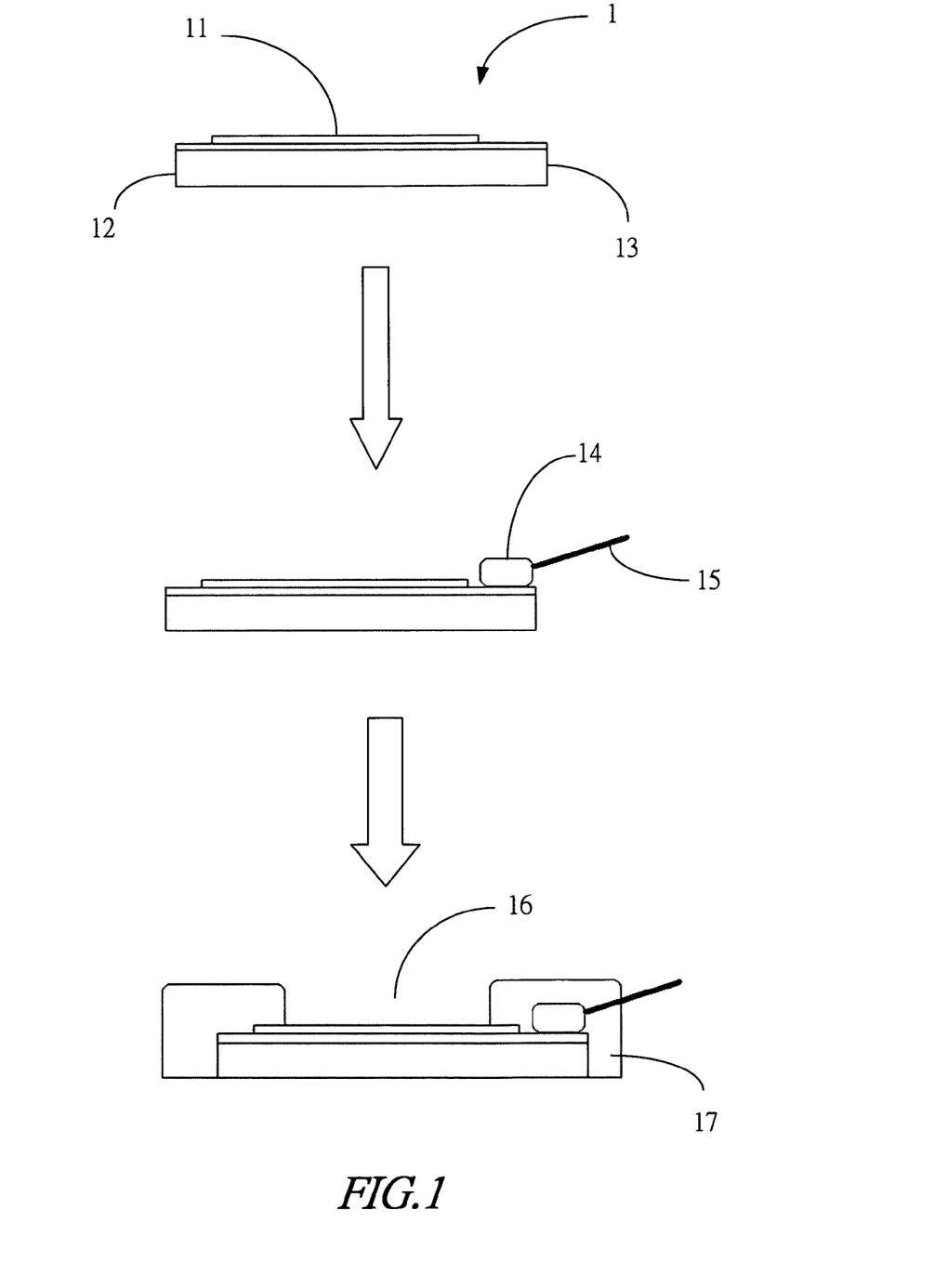
FIG. 1 shows a process diagram of an extended-gate substrate of a potassium/sodium ion sensing device applying an extended-gate field effect transistor according to the present invention.
Figure 2:
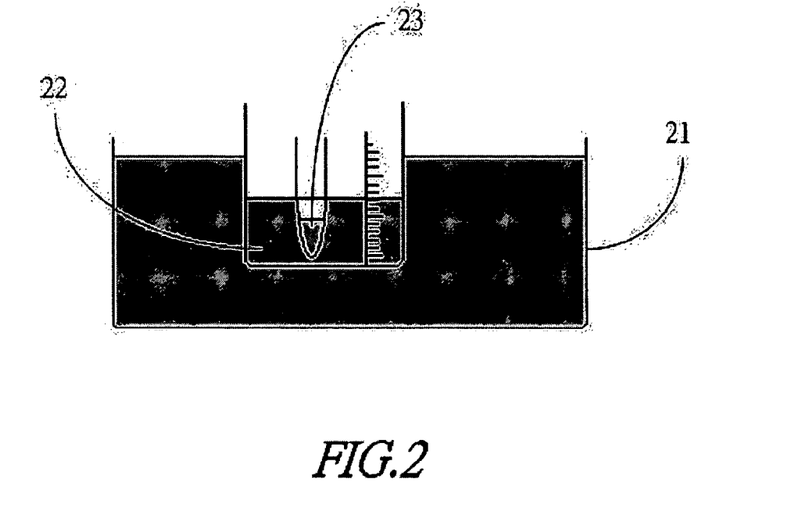
FIG. 2 shows a processing diagram of a potassium/sodium ion sensing device applying an extended-gate field effect transistor according to the present invention which the hydro-aliphatic urethane diacrylate (EB2001) intermixes with ionophores.
Figure 3:
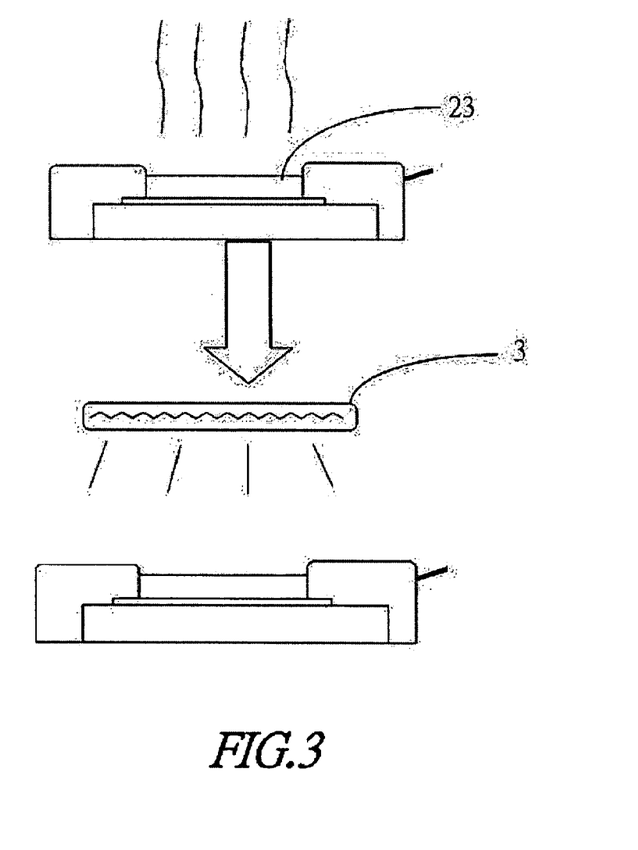
FIG. 3 shows the diagram of the steps for immobilizing a polymer ion selective membrane of a potassium/sodium ion sensing device applying an extended-gate field effect transistor according to the present invention.

The process steps of a potassium/sodium ion sensing device applying an extended-gate field effect transistor according to the present invention are described as follows:

Step 1: Fabricating $SnO_2$ solid-state film: As shown in FIG. 1, the ITO film (12) of a commercialized glass substrate (13) which has thickness 230 Å, resistance 50.100Ω/□; wherein the conditions for fabricating a $SnO_2$ film are: using sputtering to grow a $SnO_2$ film (11), $SnO_2$ as target, introducing a mixed gas which the ratio of Argon and oxygen is 4:1, during growing a $SnO_2$ film (11), keeping the temperature of the substrate on 150° C., deposition pressure 20 mtorr, radio-frequency power 50 W, plated film thickness 2000 Å;

Step 2: Fabricating a $SnO_2$/ITO glass extended sensing electrode: clearing the device (1) with methyl alcohol for 15 minutes, de-ionized water for 15 minutes, and using silver paste (14) to immobilize the conducting wire (15), and then baking for 30 minutes at 150° C., and finally sealed by the epoxy resin (17). Opening a 4 $mm^2$ sensing window (16), and again baking for 15 minutes at 150° C.;

Step 3: Fabricating a potassium ion selective electrode: As shown in FIG. 2, intermixing the hydro-aliphatic urethane diacrylate (EB2001) 1 g with photoinitiator (TPO) 0.02 g and tetrahydrofuran (THF) 1 ml, oscillated for 30 minutes by a ultrasonic bath (21); extracting a polymer solution 33 μl (33 mg) to mix with a potassium ionophore (valinomycin) 6 mg and a electronegative potassium ion complex (Potassium terakis(p-chlorophenyl) borate) 3 mg and are placed into a test tube as a polymer ion selective membrane mixture (23), and heating with a water (22) separation tank, oscillated for 60 minutes by an ultrasonic bath (21); subsequently, as shown in FIG. 3, extracting a polymer ion selective membrane mixture (23) 3 μl to be immobilized on the sensing window (16) of $SnO_2$/ITO glass pH sensing electrode, and thus obtaining a polymer ion selective electrode; still for 10 minutes, after tetrahydrofuran (THF) evaporated to stabilize the immobilized polymer ion selective membrane (18), placed into a UV cabinet (3), keeping 5 cm away from light-tube, photocuring 60 seconds with wave length 350 nm/96 W.

Step 4: Fabricating a sodium ion selective electrode: As shown in FIG. 2, intermixing hydro-aliphatic urethane diacrylate (EB2001) 1 g with photoinitiator (TPO) 0.02 g and tetrahydrofuran (THF) 1 ml, oscillated for 30 minutes by an ultrasonic bath (21); extracting a polymer solution 33 μl (33 mg) to mix with a sodium ionophore {Bis[(12-crown-4)-methyl]-dodecylmethyl malonate}4 mg and a electronegative sodium ion complex (Sodium tetrakis(4-fluorophenyl) borate dihydrate) 2.4 mg and are placed into a test tube as a polymer ion selective membrane mixture (23), and heating with a water (22) separation tank, oscillated for 60 minutes by a ultrasonic bath (21); subsequently, as shown in FIG. 3, extracting a polymer ion selective membrane mixture (23) 3 μl to be immobilized on the sensing window (16) of $SnO_2$/ITO glass pH sensing electrode, and thus obtaining a polymer ion selective membrane; still for 10 minutes, after tetrahydrofuran (THF) evaporated to stabilize the immobilized polymer ion selective membrane (18), placed into a UV cabinet (3), keeping 5 cm away from light-tube, photocuring for 180 seconds with wave length 350 nm/96 W.

Figure 4:
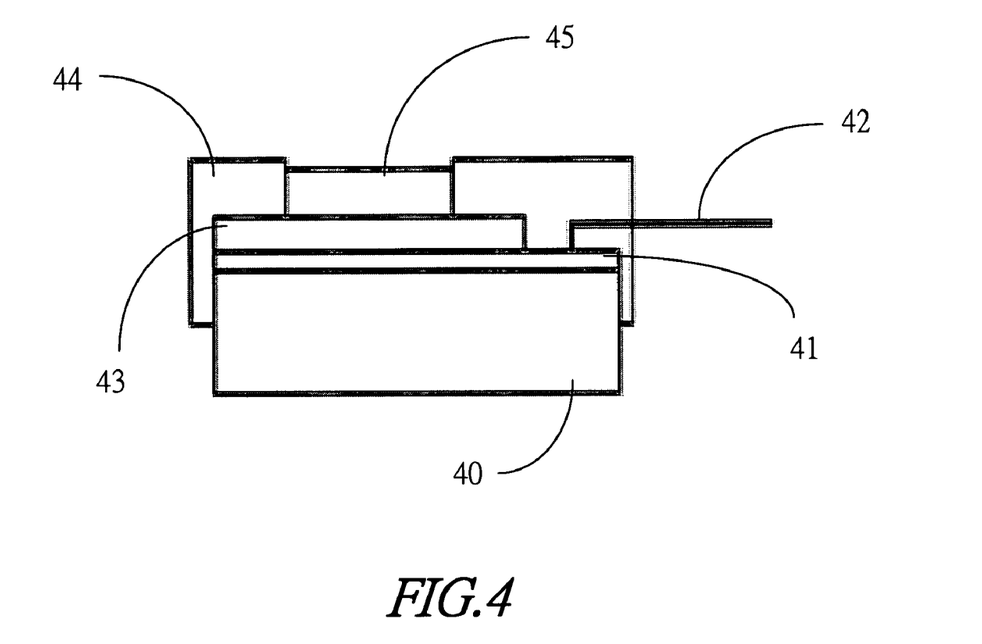
FIG. 4 shows the cross section view of a potassium/sodium ion sensing device applying an extended-gate field effect transistor according to the present invention after immobilizing an ion selective membrane to a $SnO_2$/ITO/glass sensing architecture.

Step 5: As shown in FIG. 4, the architecture of a potassium/sodium ion selective electrode is: depositing a ITO film (41) on a glass substrate (40), fixing a conducting wire (42) on the ITO film (41), depositing a $SnO_2$ film (43) on the ITO film (41), sealing with epoxy resin (44), fixed a window(4 $mm^2$) by a potassium/sodium ion selective membrane (45), and thus achieving an architecture of a potassium/sodium ion sensing device applying an extended-gate field effect transistor.

Figure 5:
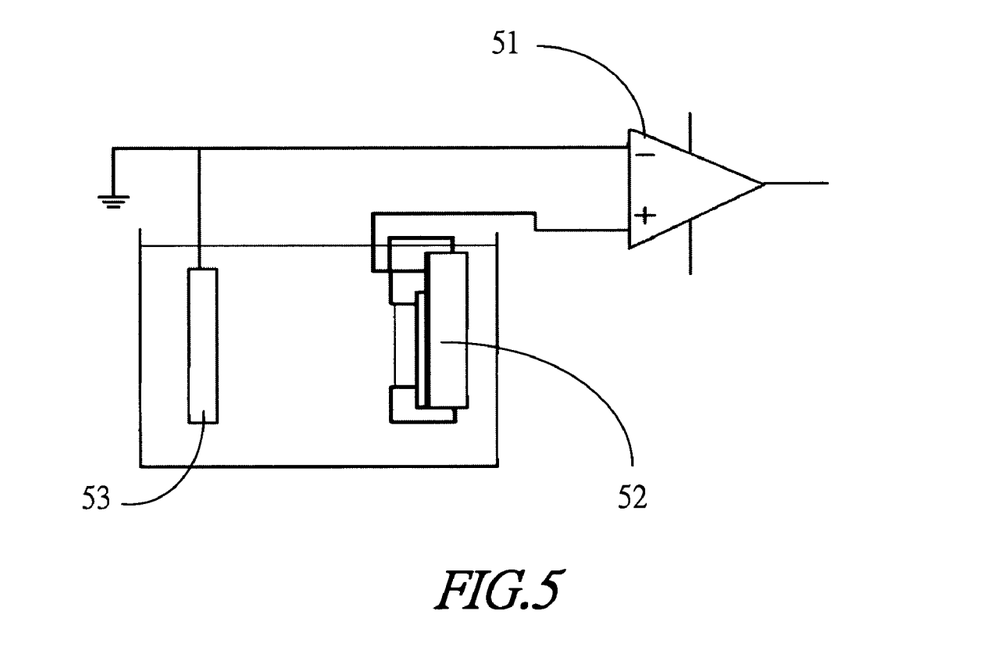
FIG. 5 shows the measurement architecture diagram of a potassium/sodium ion sensing electrode of a potassium/sodium ion sensing device applying an extended-gate field effect transistor according to the present invention.

As the measurement specification of a potassium/sodium ion sensing device applying an extended-gate field effect transistor according to the present invention, wherein FIG. 4 shows the electrode specification and the architecture of potassium/sodium ion selective electrode is: depositing a $SnO_2$ film (43) on a glass substrate (40), fixing a conducting wire (42) on the $SnO_2$ film (43), depositing a $SnO_2$ film (43) on a ITO film (41), sealing with epoxy resin (44), fixed a window (4 $mm^2$) by a potassium/sodium ion selective membrane (45), and thus obtaining an architecture of a potassium/sodium ion sensing device applying an extended-gate field effect transistor; and the measurement architecture is, as shown in FIG. 5, a single LT1167 instrumental amplifier (51) as readout circuit that a negative input connects to a reference electrode (53), a positive input connects to a potassium/sodium ion selective electrode (52), both placed into a buffer solution for measurement.

If using Tri-HCl, Tris(hydroxymethyl)aminomethane-HCl, concentration 0.05M, as a buffer solution, to prepare 5 bottles of KCL, each has concentration pK1, pK2, pK3, pK4, pK5, and then 0.01 M NaCl adding to each bottle, measuring a detected limit, the detected limit divided by 0.01 to get a sodium ion interference constant ($K_{K,Na}^{pot}$) of a potassium/sodium ion sensing device applying a extended-gate field effect transistor according to the present invention. The $K_{K,Na}^{pot}$ of this example is 1.132.

Figure 7:
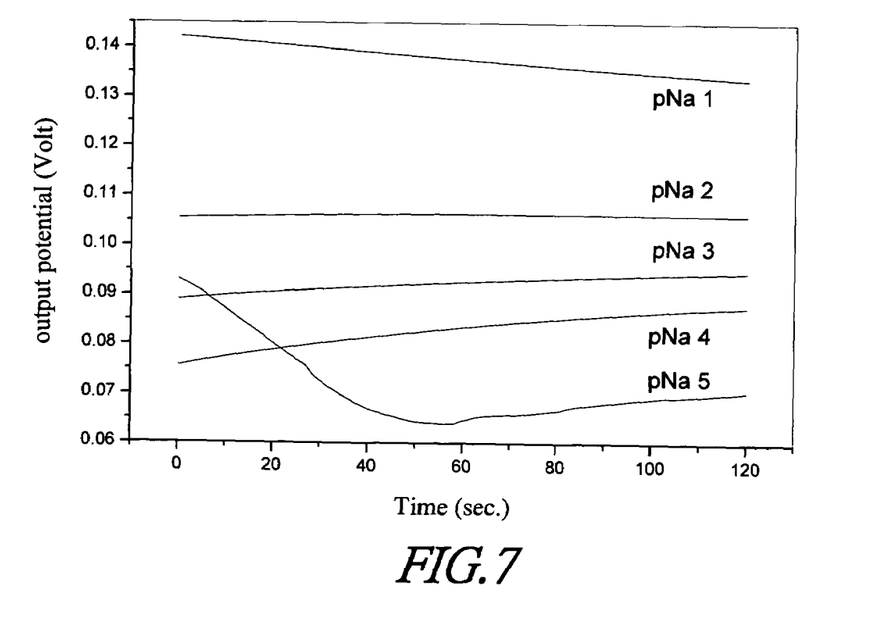
FIG. 7 shows a potential vs. time relationship diagram of a potassium/sodium ion sensing device applying an extended-gate field effect transistor according to the present invention which using the hydro-aliphatic urethane diacrylate (EB2001) to encapsulate a sodium ionophore to measure a sodium ion buffer solution.

If using Tri-HCl, Tris(hydroxymethyl)aminomethane-HCl, concentration 0.05M, as the buffer solution, to prepare 5 bottles of NaCl, each has concentration pNa0.1, pNa1, pNa2, pNa3, pNa4, as measurement architecture to perform measurements, to obtain the measured result as shown in FIG. 7; If using Tri-HCl, Tris(hydroxymethyl)aminomethane-HCl, concentration 0.05M, as a buffer solution, to prepare 5 bottles of NaCl, each has concentration pNa0.1, pNa1, pNa2, pNa3, pNa4, and then 0.01 M KCl adding to each bottle, measuring a detected limit, the detected limit divided by 0.05 to get a potassium ion interference constant ($K_{Na,K}^{pot}$) of a potassium/sodium ion sensing device applying an extended-gate field effect transistor according to the present invention. The $K_{Na,K}^{pot}$ of this example is $10^{-2.38}$.

As a potassium/sodium ion sensing device applying an extended-gate field effect transistor according to the present invention used for mutually correcting the measurement of potassium/sodium ion selective electrodes, FIG. 4 shows the electrode specification, the architecture of a potassium/sodium ion selective electrode is: depositing a ITO film (41) on a glass substrate (40), fixing a conducting wire (42) on the ITO film (41), depositing a $SnO_2$ film (43) on the ITO film (41), sealing with epoxy resin (44), fixing a window (4 $mm^2$) by a potassium/sodium ion selective membrane (45), and thus obtaining an architecture of a potassium/sodium ion sensing device applying an extended-gate field effect transistor; and the measurement architecture is, as shown in FIG. 5, a single LT1167 signal amplifier (51) as a readout circuit, a negative input connects to a reference electrode (53), positive input connects to a potassium/sodium ion selective electrode (52), both placed into a buffer solution for measurement.

Figure 10:
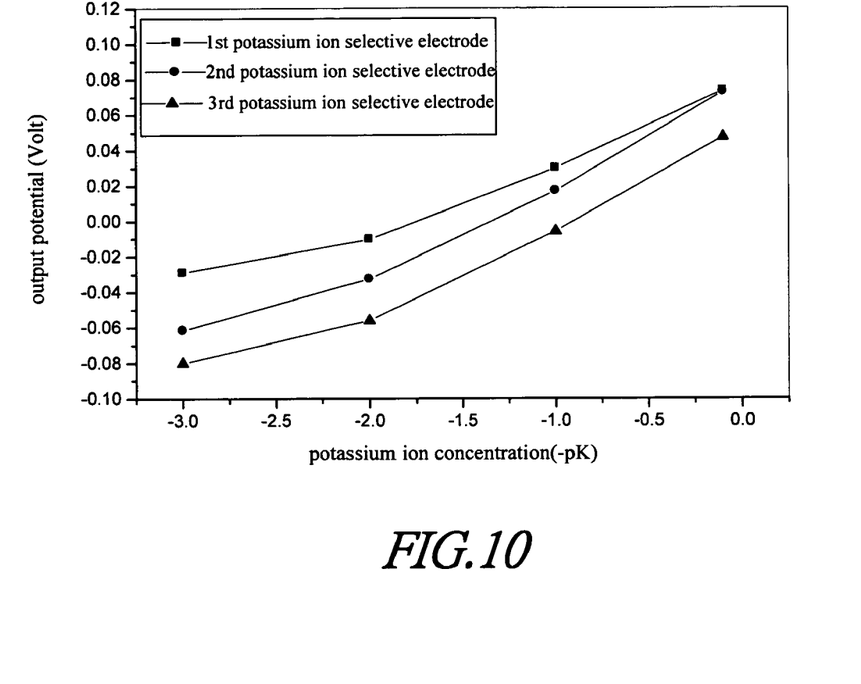
FIG. 10 shows the correction curve plot of a potassium/sodium ion sensing device applying an extended-gate field effect transistor according to the present invention which using a potassium ion electrode to measure a KCL(pK0–3) solution.

If using Tri-HCl, Tris(hydroxymethyl) aminomethane-HCl, concentration 0.05M, as a buffer solution, to prepare 5 bottles of KCL, each has concentration pK1, pK2, pK3, pK4, pK5, all measured by the potassium ion selective electrode of a potassium/sodium ion sensing device applying an extended-gate field effect transistor according to the present invention to obtain a correction plot as shown in FIG. 10.

Figure 11:
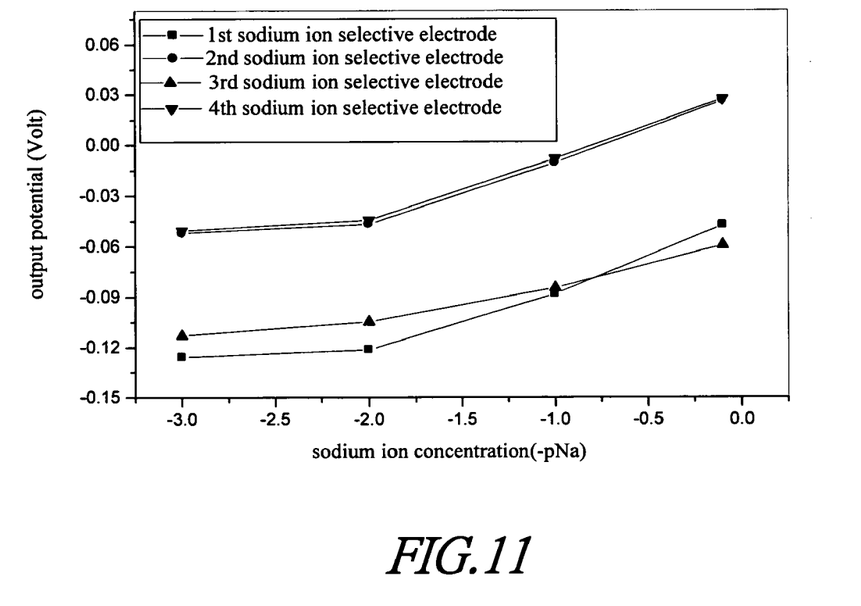
FIG. 11 shows the correction curve plot of a potassium/sodium ion sensing device applying an extended-gate field effect transistor according to the present invention which using a sodium ion electrode to measure a NaCl(pNa0–3) solution.

If using Tri-HCl, Tris(hydroxymethyl) aminomethane-HCl, concentration 0.05M, as a buffer solution, to prepare 5 bottles of NaCl, each has concentration pNa0.1, pNa1, pNa2, pNa3, pNa4, all measured by the sodium ion selective electrode of a potassium/sodium ion sensing device applying an extended-gate field effect transistor according to the present invention to obtain a correction plot as shown in FIG. 11.

Figure 12:
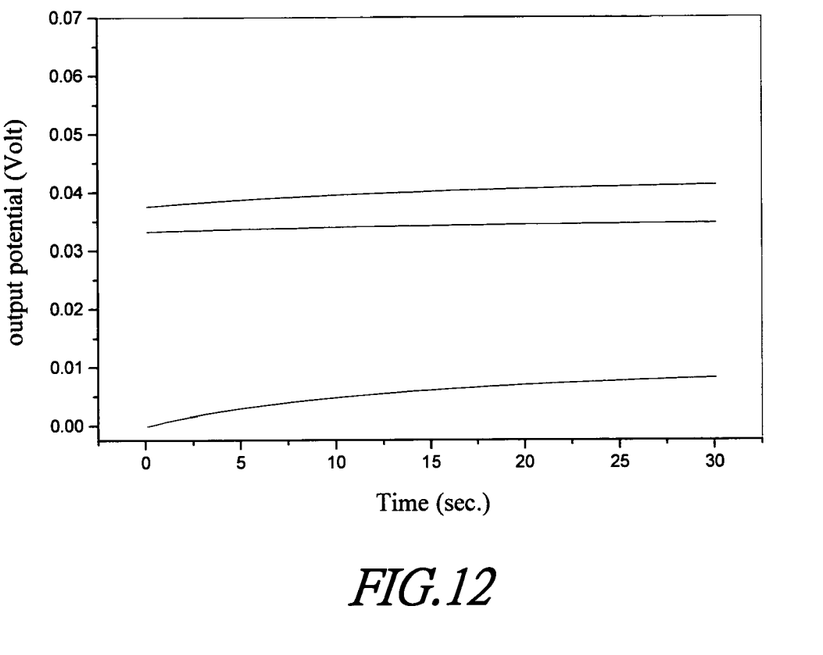
FIG. 12 shows the output potential plot which a potassium ion electrode of a potassium/sodium ion sensing device applying an extended-gate field effect transistor according to the present invention is used to measure an unknown(pNa 1, pK 1.3) solution.
Figure 13:
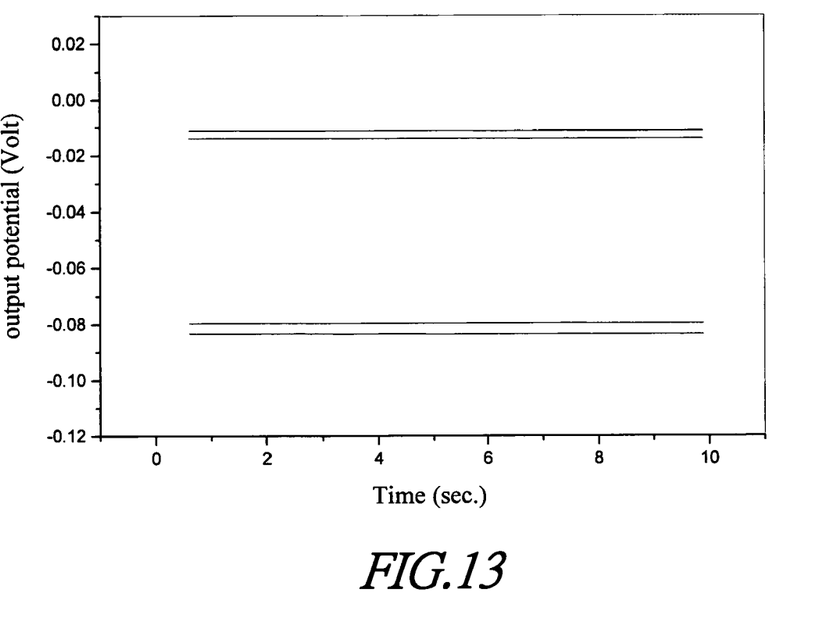
FIG. 13 shows the output potential plot which a sodium ion electrode of a potassium/sodium ion sensing device applying an extended-gate field effect transistor according to the present invention is used to measure an unknown (pNa 1, pK 1.3) solution.

If using Tri-HCl, Tris(hydroxymethyl) aminomethane-HCl, concentration 0.05M, as the buffer solution, to prepare NaCl 1M and KCl 0.05M in a bottle, measured by the potassium ion selective electrode of a potassium/sodium ion sensing device applying an extended-gate field effect transistor according to the present invention to obtain an output potential plot as shown in FIG. 12, and measured by the sodium ion selective electrode of a potassium/sodium ion sensing device applying an extended-gate field effect transistor according to the present invention to obtain a output potential plot as shown in FIG. 13.

The equation $10^{E\text{-}constant/m} = a_K - K_{K,Na}^{pot} a_{Na}$ can be satisfied by the correction plot of potassium ion selective electrode as shown in FIG. 10 and the output potential of potassium concentration.

The equation $10^{E\text{-}constant/m} = a_{Na} - K_{Na,K}^{pot} a_K$ can be satisfied by the correction plot of sodium ion selective electrode as shown in FIG. 11 and the output potential of sodium concentration.

The corrected potassium and sodium ion concentration can be jointly determined by the above-mentioned equations $10^{E\text{-}constant/m} = a_K - K_{K,Na}^{pot} a_{Na}$ and $10^{E\text{-}constant/m} = a_{Na} - K_{Na,K}^{pot} a_K$, as shown in table 1.

TABLE 1

Results of corrected potassium/sodium
ion vs results of uncorrected

|  | Actual value | Uncorrected result | Corrected result |
|---|---|---|---|
| Sodium ion | pNa 1 | pNa = 1.018 | pNa = 1.018 |
| Potassisum ion | pK 1.3 | pK = 0.7816 | pK = 1.248 |

The above table 1 shows the comparison of corrected result and uncorrected result of potassium/sodium ions which using sodium ion selective electrode to correct potassium ion selective electrode, the error rate of potassium ion selective electrode before correction is 39.8%, the error rate of potassium ion selective electrode after correction is 4%, therefore this table illustrates the way of the potassium and sodium ion selective electrodes correcting each other can be used to obtain a result that more close to the actual value.

Referring to FIG. 4, shows the cross section view of a potassium/sodium ion sensing device applying an extended-gate field effect transistor according to the present invention after immobilizing an ion selective membrane to a $SnO_2$/ITO/glass sensing architecture. As seen from the drawing, it is easy and capable of meeting CMOS standard process to fabricate an extended-gate ion sensitive field effect transistor (EGFET); the ion selective membrane is: using the hydro-aliphatic urethane diacrylate (EB2001) as substrate, photo-curable, easily microminaturization that facilitate fabricating multiple ion sensors, such a structure do not need a redox layer of polymer to stabilize the response signal, just use the good transparency of a simple hydrophile polymer to read signals steadily, and thus an ion sensing electrode with a simple process can be achieved.

Figure 6:
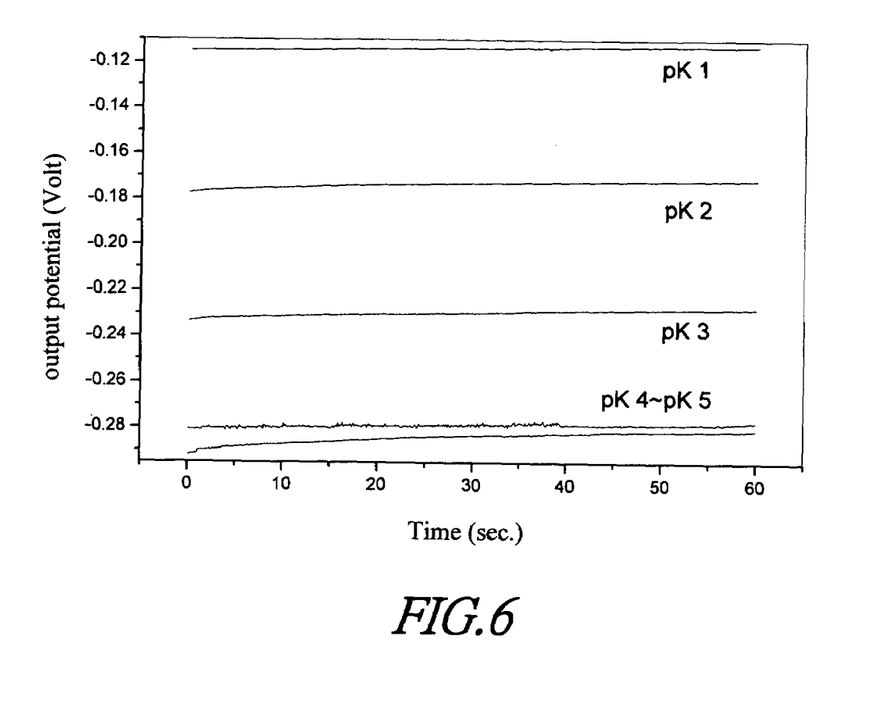
FIG. 6 shows a potential vs. time relationship diagram of a potassium/sodium ion sensing device applying an extended-gate field effect transistor according to the present invention which using the hydro-aliphatic urethane diacrylate (EB2001) to encapsulate a potassium ionophore to measure a potassium ion buffer solution.

Referring to FIG. 5, shows the measurement architecture diagram of a potassium/sodium ion sensing electrode of a potassium/sodium ion sensing device applying an extended-gate field effect transistor according to the present invention; As illustrated in the drawing, the present invention do not need to add a wave filter circuit, and the measurement results in FIG. 6 and FIG. 7 can be obtained.

Figure 8:
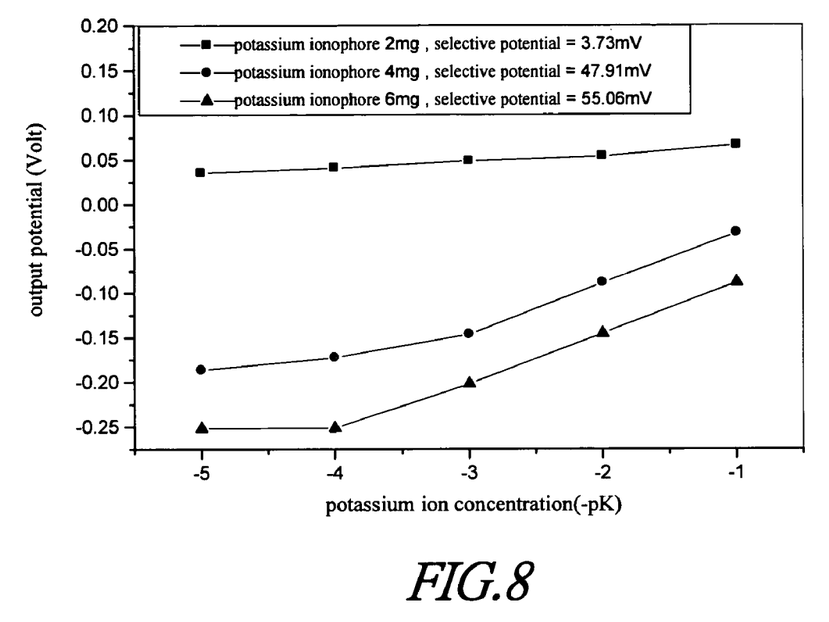
FIG. 8 shows a measured signal diagram of a potassium/sodium ion sensing device applying an extended-gate field effect transistor according to the present invention in which the concentration range of the potassium ion is between pK1–pK5 after a potassium ionophore is intermixed with the hydro-aliphatic urethane diacrylate (EB2001) 33 mg.

FIG. 8 shows a measured signal diagram of a potassium/sodium ion sensing device applying an extended-gate field effect transistor according to the present invention during the concentration range of the potassium ion is between pK1–pK5 after a potassium ionophore intermixed with the hydro-aliphatic urethane diacrylate (EB2001) 33 mg; As seen from the drawing, the hydro-aliphatic urethane diacrylate (EB2001) as substrate encapsulating a potassium ionophore (valinomycin) and a electronegative potassium ion complex (Potassium terakis(p-chlorophenyl)borate), immobilized on a $SnO_2$ film, the potassium ion solution concentration is measured; when the ratio of the potassium ionophore to the hydro-aliphatic urethane diacrylate (EB2001) is 6:33(w/w) and the potassium ion concentration range is 0.1~10–4M, the selective potential is about 55.06 mV.

Figure 9:
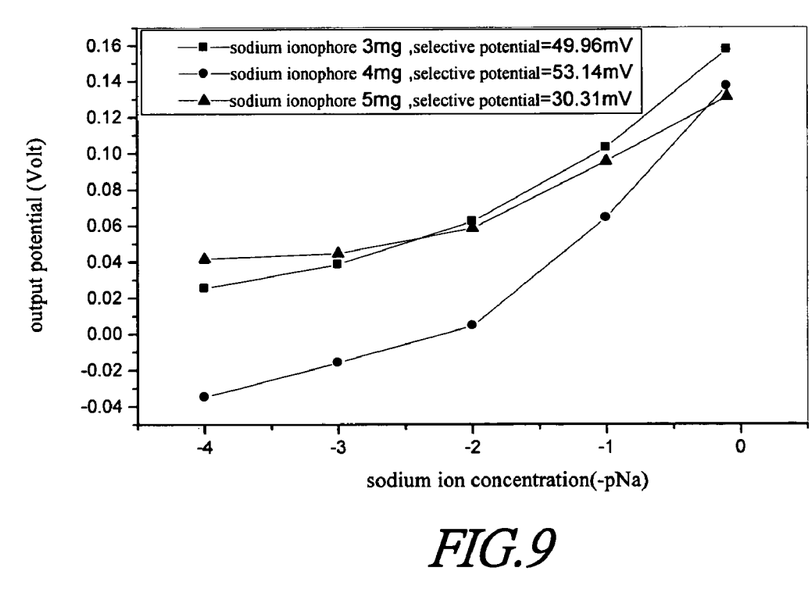
FIG. 9 shows a measured signal diagram of a potassium/sodium ion sensing device applying an extended-gate field effect transistor according to the present invention in which the concentration range of the sodium ion is between pNa0–pNa4 after a sodium ionophore is intermixed with the hydro-aliphatic urethane diacrylate (EB2001) 33 mg.

FIG. 9 shows a measured signal diagram of a potassium/sodium ion sensing device applying an extended-gate field effect transistor according to the present invention during the concentration range of the sodium ion is pNa0–pNa4 after sodium ionophore intermixed with a hydro-aliphatic urethane diacrylate (EB2001) 33 mg. As seen in the drawing, the hydro-aliphatic urethane diacrylate (EB2001) as substrate encapsulating sodium ionophore {Bis[(12-crown-4) methyl]-dodecylmethyl malonate} and a electronegative sodium ion complex (Sodium tetrakis(4-fluorophenyl) borate dehydrate), immobilized on a $SnO_2$ film, the sodium ion solution concentration is measured; when the ratio of sodium ionophore to the hydro-aliphatic urethane diacrylate (EB2001) is 4:33(w/w) and the potassium ion concentration range is 0.1~10–4M, the selective potential is about 53.14 mV.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A manufacturing method of a potassium/sodium ion sensing device applying an extended-gate field effect transistor, the method comprising the steps of:
    Step 1: depositing a $SnO_2$ thin film on an ITO glass substrate as a solid-state sensing substrate;
    Step 2: adhering a silver paste to said ITO glass substrate and a conducting wire;
    Step 3: using epoxy resin to seal said silver paste and said conducting wire, and to package a sensing window;
    Step 4: forming a polymer ion selective membrane including a photo-curable polymer, a photo-initiator, a electronegative additive, a potassium ionophore or sodium ionophore by the steps of:
        Step (a): intermixing a hydro-aliphatic urethane diacrylate (EB2001) with a photo-initiator;
        Step (b): adding a photo-curable polymer into the mixture of step (a) and intermixing in an ultrasonic bath;
        Step (c): adding a potassium ionophore or sodium ionophore, an electronegative additive into the mixture of step (b);
        Step (d): intermixing the mixture of step (c) in an ultrasonic bath;
    Step 5: immobilizing said polymer ion selective membrane in said sensing window.

2. The manufacturing method as recited in claim 1, wherein said ITO glass substrate that an ITO thin film with thickness 230 Å and resistance 50~100Ω/□ is provided on a glass substrate.

3. The manufacturing method as recited in claim 1, wherein using sputtering to grow a $SnO_2$ thin film, $SnO_2$ as target, introducing a mixed gas that the ratio of argon to oxygen is 4:1.

4. The manufacturing method as recited in claim 1, wherein maintaining the temperature of said ITO glass substrate to be 150° C., deposition pressure 20 mtorr, radio-frequency power 50 W, plated film thickness 2000 Å during growing said $SnO_2$ thin film.

5. The manufacturing method as recited in claim 1, wherein said potassium/sodium ion sensing device applying an extended-gate field effect transistor cleaned by methyl alcohol for 15 minutes, de-ionized water for 15 minutes, uses said silver paste to immobilize said conducting wire, and then baked 30 minutes at 150° C.

6. The manufacturing method as recited in claim 1, wherein said potassium/sodium ion sensing device applying an extended-gate field effect transistor is sealed with epoxy resin, and baked for 10 minutes at 150° C.

7. The manufacturing method of claim 1, wherein the ratio of the hydro-aliphatic urethane diacrylate (EB2001) to the photo-initiator is 100:2(w/w).

8. The manufacturing method of claim 1, wherein said photo-curable polymer placed in the ultrasonic bath is mixed for 30 minutes.

9. The manufacturing method of claim 1, wherein the ratio between said hydro-aliphatic urethane diacrylate (EB2001) and said potassium ionophore and said electronegative potassium ion complex is 33:6:3(w/w).

10. The manufacturing method of claim 1, wherein the ratio between said hydro-aliphatic urethane diacrylate (EB2001) and said sodium ionophore and said electronegative sodium ion complex is 33:4:2.4(w/w).

11. The manufacturing method of claim 1, wherein intermixing said hydro-aliphatic urethane diacrylate (EB2001) with said potassium ionophore and said electronegative potassium ion complex and placed in an ultrasonic bath, heating in a 30° C. water separation tank, oscillating and mixing for 1 hour.

* * * * *